United States Patent
Lake, Jr. et al.

(10) Patent No.: US 7,282,186 B2
(45) Date of Patent: Oct. 16, 2007

(54) DECONTAMINATION DEVICE

(76) Inventors: Robert F. Lake, Jr., 3757 NW. 5th Ave., Boca Raton, FL (US) 33431; Jeffrey S. Tennant, 860 SW. 20th St., Boca Raton, FL (US) 33486

( * ) Notice: Subject to any disclaimer, the term of this patent is extended or adjusted under 35 U.S.C. 154(b) by 339 days.

(21) Appl. No.: 10/600,280

(22) Filed: Jun. 20, 2003

(65) Prior Publication Data

US 2004/0258560 A1 Dec. 23, 2004

(51) Int. Cl.
*A61L 2/00* (2006.01)
(52) U.S. Cl. .................. 422/300; 206/205; 239/274
(58) Field of Classification Search ................ 422/300, 422/292, 1, 28; 239/274; 206/205
See application file for complete search history.

(56) References Cited

U.S. PATENT DOCUMENTS

| 5,641,464 | A | * | 6/1997 | Briggs et al. ............... 422/300 |
| 5,683,655 | A | * | 11/1997 | Carter ......................... 422/28 |
| 5,722,537 | A | * | 3/1998 | Sigler ......................... 206/205 |
| 5,892,233 | A | * | 4/1999 | Clement ................ 250/455.11 |
| 6,499,560 | B1 | | 12/2002 | Lang et al. |

* cited by examiner

*Primary Examiner*—Krisanne Jastrzab
(74) *Attorney, Agent, or Firm*—Akerman Senterfitt; Gregory A. Nelson

(57) ABSTRACT

A decontamination device for decontaminating medical apparatus includes a housing and a dispenser within the housing for contacting a portion of the medical apparatus with a decontaminating compound when the portion of the medical apparatus is placed within the housing. Structure for removably engaging the housing to the medical apparatus is provided. The decontamination device can be used with many different medical apparatus, such as stethoscopes. A method for decontaminating medical apparatus is also provided.

19 Claims, 6 Drawing Sheets

DECONTAMINATION DEVICE

STATEMENT REGARDING FEDERALLY SPONSORED RESEARCH OR DEVELOPMENT

Not applicable.

FIELD OF THE INVENTION

This invention relates generally to medical apparatus and, more particularly, to decontamination devices for medical apparatus.

BACKGROUND OF THE INVENTION

The transmission of infectious disease is a matter of increasing concern among healthcare professionals. It has long been known that medical instruments must be decontaminated, in order to prevent the spread of infectious disease among different patients with whom the medical apparatus comes in contact. Decontamination includes the removal of foreign material such as chemical or radiological contaminants, as well as sterilization and disinfection. Sterilization is a form of decontamination in which all forms of microbial life are killed. Disinfection is a relative term meaning that the microbial burden of an instrument is reduced but not eliminated. Some medical apparatus, such as stethoscopes, are decontaminated only infrequently. The design, construction, and expense of the device can impede decontamination procedures. Decontamination of medical apparatus usually requires time consuming procedures or special equipment, which further reduces the likelihood that the medical apparatus will be decontaminated after each and every use. In order to avoid the need for decontamination, the medical industry has increasingly utilized disposable devices or devices with disposable portions, such as covers.

SUMMARY OF THE INVENTION

A decontamination device for decontaminating, such as disinfecting or sterilizing, surface portions of medical apparatus includes a housing. A dispenser/storage means within the housing is provided for contacting a portion of the surface of the medical apparatus with a decontaminating compound when the portion of the medical apparatus is placed within the housing. Structure is provided for removably engaging the housing to the medical apparatus.

The structure for detachably engaging the housing to the medical apparatus can be snap-on structure for engaging a portion of the medical apparatus. The snap-on structure can be an elastically deformable, inwardly directed protrusion on the housing which fits around a portion of the medical apparatus when that portion is placed into the housing.

The dispenser can include suitable structure for dispensing the decontaminating compound onto the portion of the medical apparatus within the housing. In one embodiment, the dispenser comprises an absorbent material having absorbed therein the decontaminating compound. The absorbent material stores and releases the decontaminating compound onto the surface of the medical apparatus when the medical apparatus contacts the absorbent material.

The decontamination device can have structure for attaching the decontamination device to the medical apparatus when the medical apparatus is in use, to prevent the decontamination device from being separated from the medical apparatus. The attachment structure can be a lanyard.

Packaging for the decontamination device can be provided. A removable cover can be provided for the housing. At least two of the decontamination devices can be detachably engaged.

The housing can comprise indicia for providing information about the decontamination device. The indicia can comprise at least one selected from the group consisting of color, printed material, and embossed material. The indicia can indicate at least one selected from the group consisting of the decontamination compound and the particular medical apparatus for which the sterilization device is intended.

The decontamination compound can be any suitable decontaminating compound. Suitable decontamination compounds include, but are not limited to the group consisting of: glutaraldehydes, such as 2% alkaline glutaraldehyde, glutaraldehyde-phenate; chlorine compounds, such as sodium hypochlorite and calcium hypochlorite; alcohols, such as 70-99% isopropyl or ethyl alcohol; iodophors, such as providone-iodine; peroxygen compounds, such as 3% stabilized hydrogen peroxide; phenolics, such as derivatives of phenol; and quaternary ammonium compounds, such as benzalkonium chloride.

The device can contain an indicator compound for indicating that the medical apparatus has been decontaminated by the decontamination device. The indicator compound can be a dye, colorant, chemical marker, or radioisotope.

The decontamination device can be adapted for use with a stethoscope. In this embodiment, the housing is dimensioned so as to receive at least a portion of the head of the stethoscope.

A method is provided for utilizing medical apparatus. A decontamination device is provided with a housing and a dispenser within the housing for contacting a portion of the medical apparatus with a decontaminating compound when the portion of the medical apparatus is placed within the housing, and structure for removably engaging the housing to the medical apparatus. A portion of the medical apparatus is placed within the housing and in contact with the dispenser. The decontaminating compound from the dispenser contacts a portion of the medical apparatus, thereby decontaminating that portion. The medical apparatus is then used, and after use is placed again into the decontamination device and engaged to the decontamination device.

BRIEF DESCRIPTION OF THE DRAWINGS

There is shown in the drawings embodiments which are presently preferred, it being understood, however, that the invention is not limited to the precise arrangements and instrumentalities shown, wherein.

DETAILED DESCRIPTION OF THE INVENTION

Figure 1:
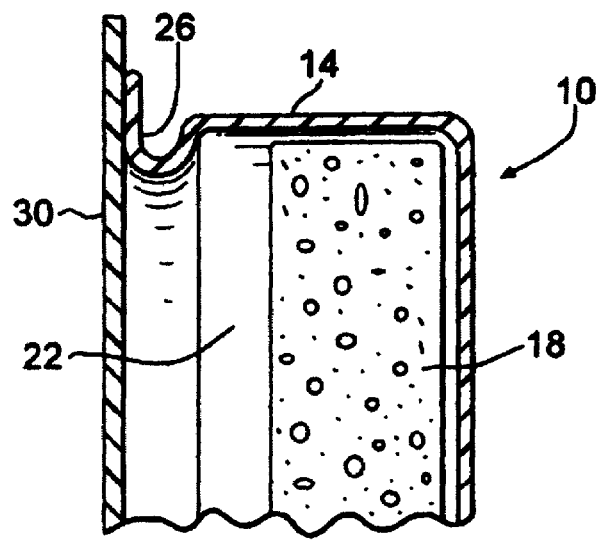
FIG. 1 is a cross-section of a decontamination device according to the invention.

There is shown is FIG. 1 a decontamination device 10 having a housing 14 and a dispenser 18. The dispenser 18 is provided in an interior 22 formed by the housing 14. Structure 26 is provided for engaging a medical apparatus. A removable cover 30 can be provided to maintain the sterility of the device when not in use, or as packaging prior to initial use.

Figure 2:
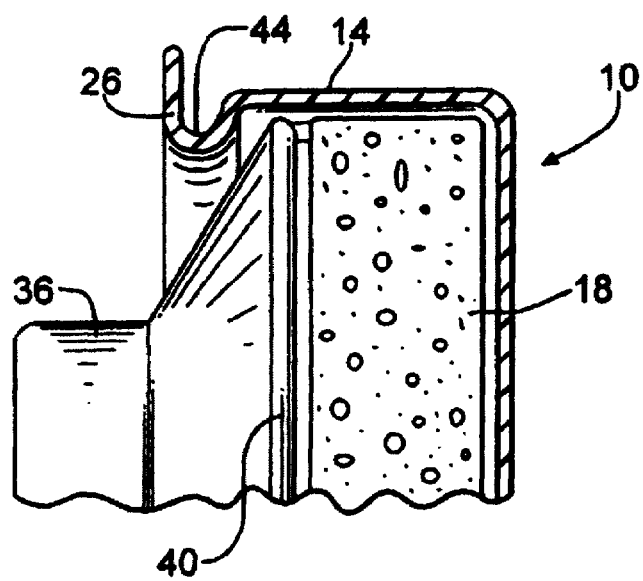
FIG. 2 is a cross-section showing the decontamination device engaged to a medical apparatus.

The housing 14 is dimensioned to receive a portion of a medical apparatus that is to be decontaminated. The invention can be utilized with many different types of medical apparatus. There is shown in FIG. 2 the head 36 of a stethoscope. The head 36 has a diaphragm 40, and the interior of housing 14 is dimensioned to receive the diaphragm 40 so that it will contact the dispenser 18.

The dispenser 18 can be of any suitable design for contacting the desired portion of the medical apparatus with the decontaminating compound. In the embodiment shown, the dispenser 18 comprises an absorbent pad which absorbs the decontaminating compound and dispenses the compound when contacted by the medical apparatus. Placement of the medical apparatus into the housing 14 causes a portion of the medical apparatus, such as diaphragm 40 of stethoscope head 36, to contact the dispenser 18 and the decontaminating compound. Other dispenser designs are possible, including various mechanical or pressurized constructions for releasing fluid when contacted.

The structure for engaging a portion of the medical apparatus can be any suitable structure. This can include cooperating tongue and groove structure, slots, snaps, fasteners, and other engagement structure. In the embodiment shown in FIG. 2, an inwardly directed protrusion 44 is formed in the housing 14. The housing 14 has suitable flexibility to permit flexing when the medical apparatus, such as a stethoscope head 36 contacts the protrusion 44. The head 36 will then interlock with the housing 14 as shown in FIG. 2.

The decontaminating compound can be any suitable compound or mixture of compounds. Such compounds include glutaraldehydes, such as 2% alkaline glutaraldehyde, glutaraldehyde-phenate; chlorine compounds, such as sodium hypochlorite and calcium hypochlorite; alcohols, such as 70-99% isopropyl or ethyl alcohol; iodophors, such as providone-iodine; peroxygen compounds, such as 3% stabilized hydrogen peroxide; phenolics, such as derivatives of phenol; and quaternary ammonium compounds, such as benzalkonium chloride.

Figure 3:
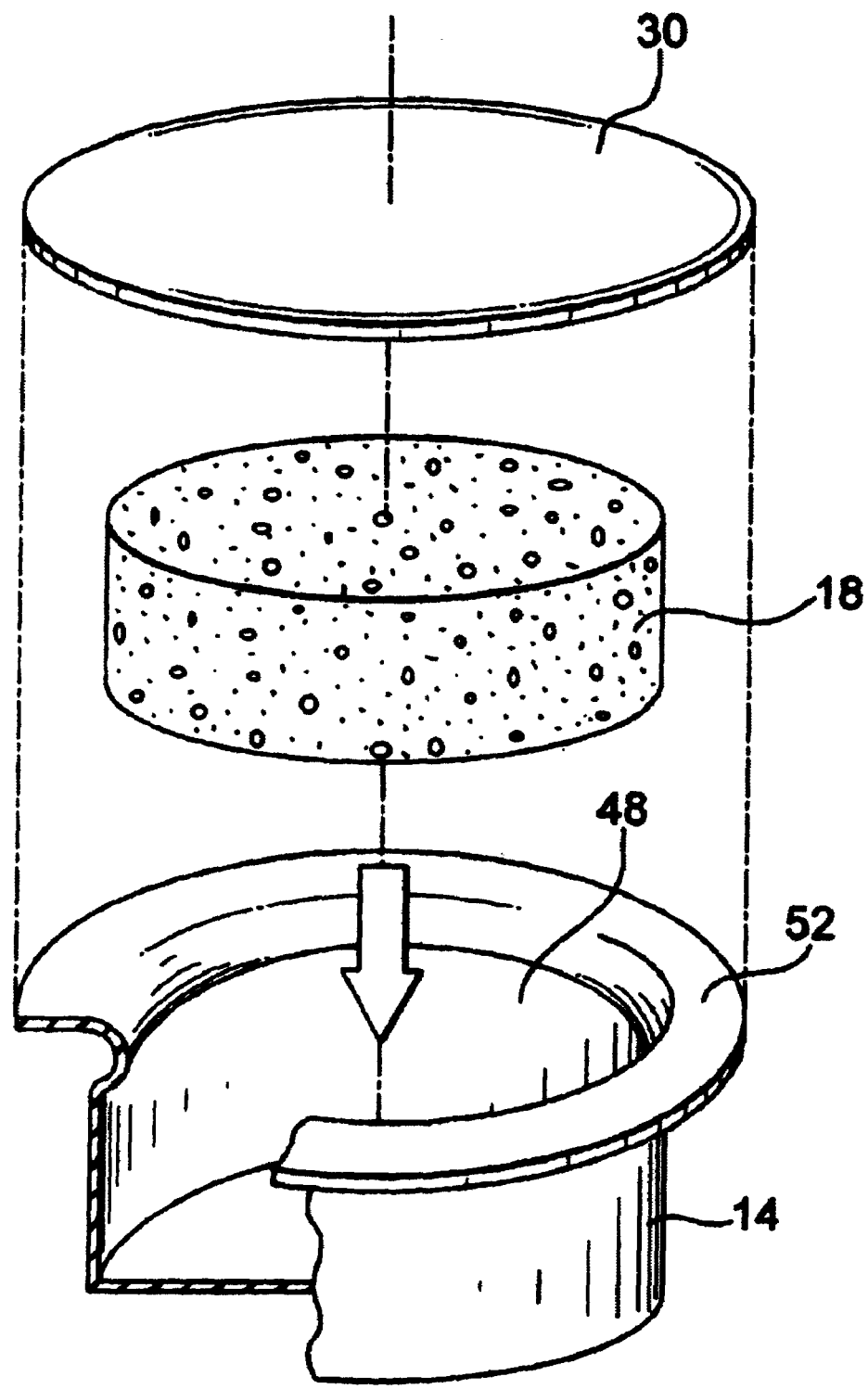
FIG. 3 is an exploded perspective view, partially broken away, of a decontamination device according to the invention.

The decontamination device can be manufactured and assembled by several different production methods. In FIG. 3 there is shown an exploded view in which the dispenser 18 is a pad and is placed in an interior 48 of the housing 14. The cover 30 is then secured to flange 52 by a suitable adhesive so as to be removable.

Figure 4:
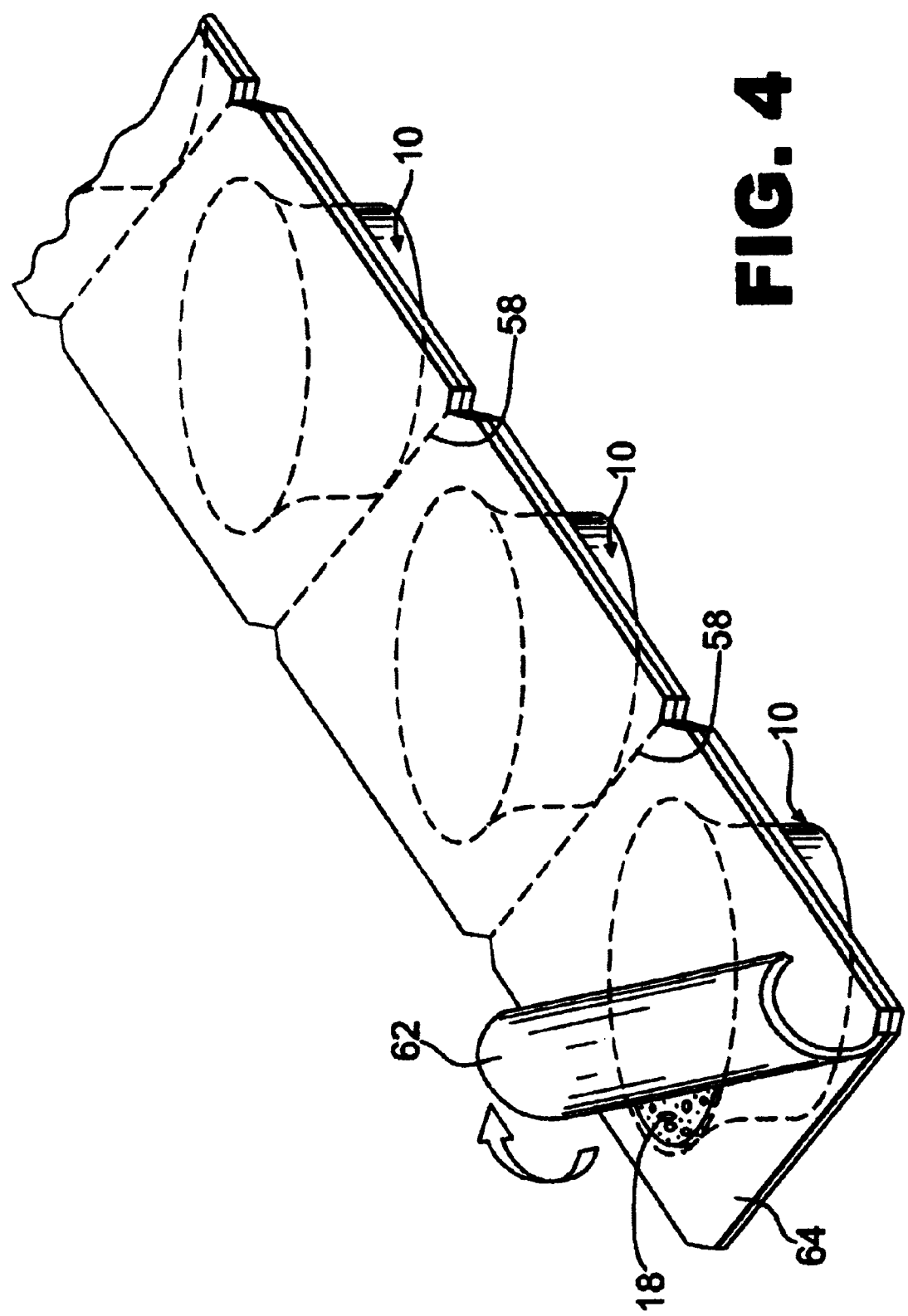
FIG. 4 is a perspective view, partially in phantom, illustrating a packaging system in which several decontamination devices are engaged together.

The invention can be packaged in many different ways. There is shown in FIG. 4 an embodiment in which several decontamination devices 10 are joined at edges 58. The edges 58 are perforated, scored, or otherwise constructed to permit the detachment of the decontamination devices from one another. Covers 62 can then be removed by peeling or otherwise removing the covers 62 from housings 64.

Figure 5:
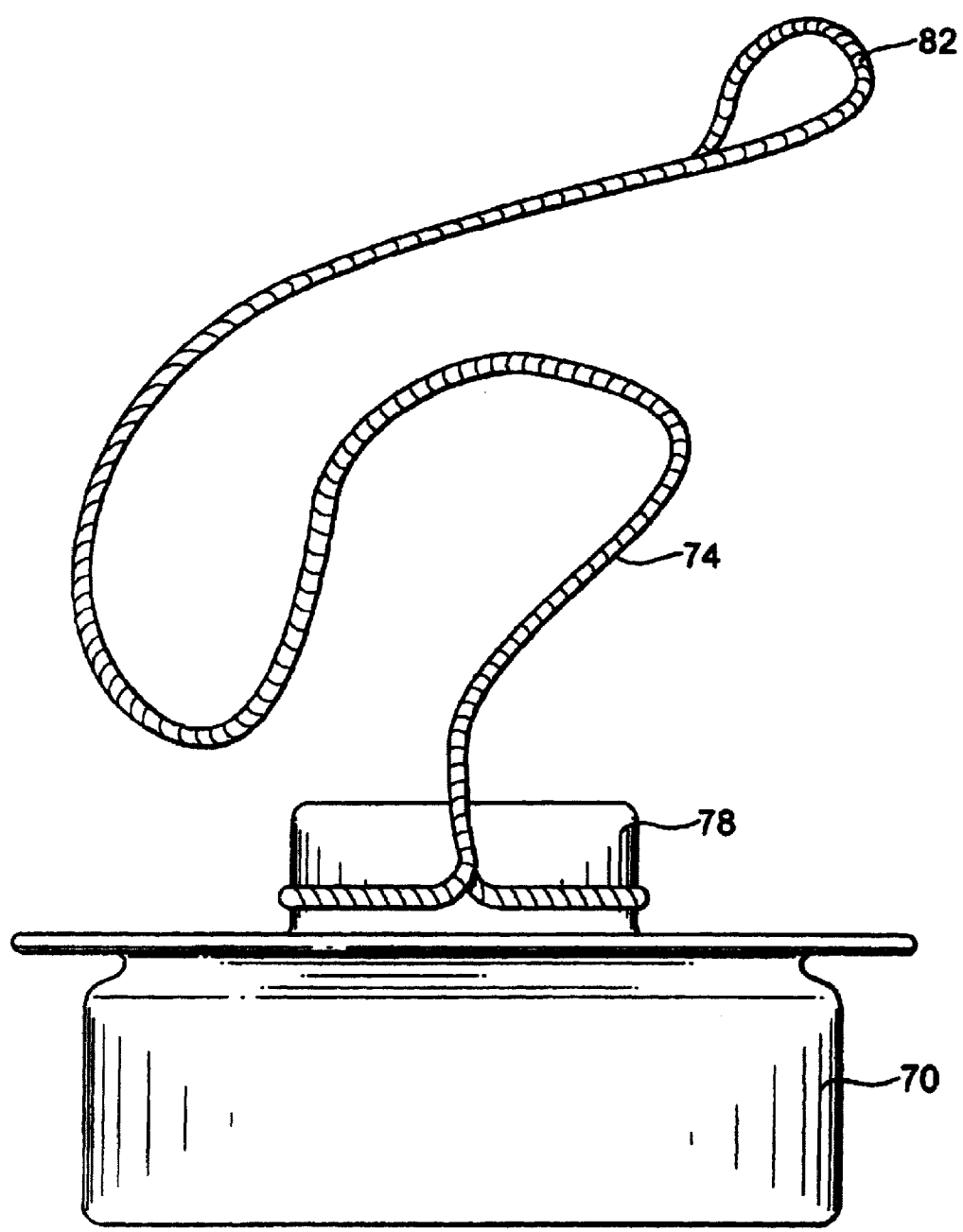
FIG. 5 is a side elevation of an alternative embodiment with structure for attaching the decontamination device to a medical apparatus.
Figure 6:
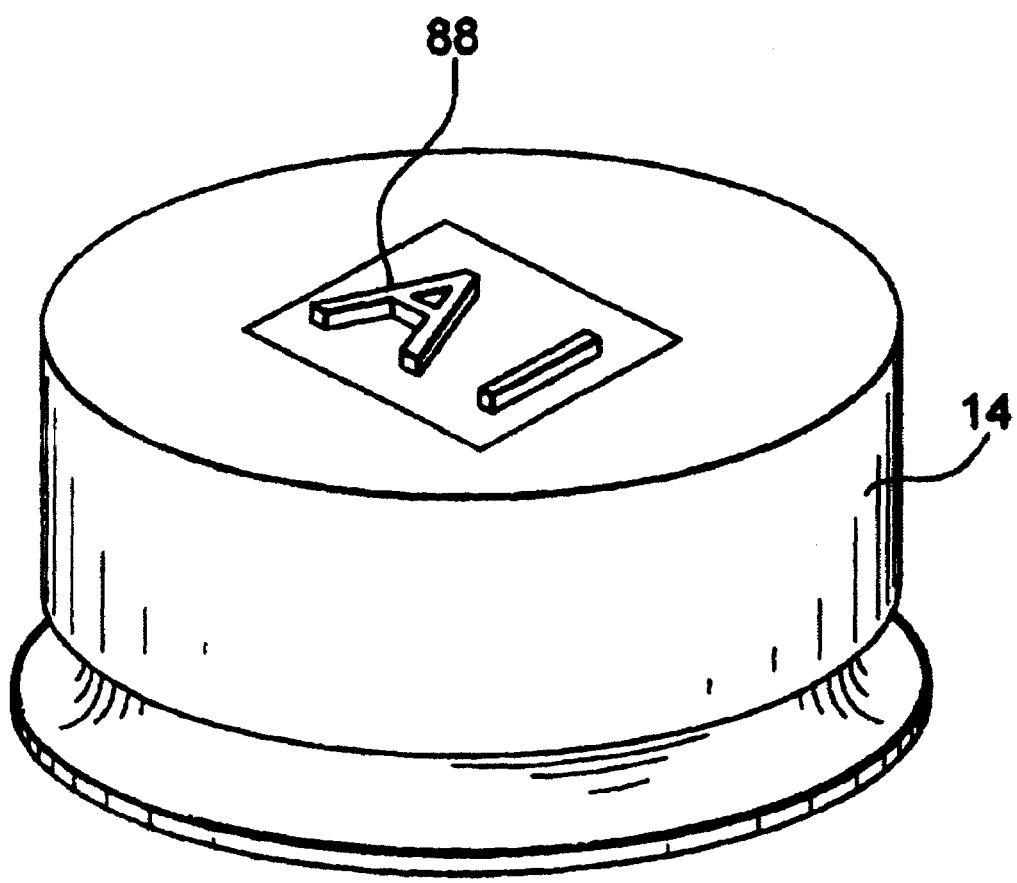
FIG. 6 is a perspective of an alternative embodiment bearing indicia for providing information about the decontamination device.

The decontamination device can be attached to the medical apparatus when in use to prevent the decontamination device from becoming separated from the medical apparatus. In the example shown in FIG. 5, the decontamination device 70 has been fitted with an attachment device such as lanyard 74 which can be secured about a suitable attachment member 78 on the decontamination device 70. Suitable structure such as loop 82 can be provided for securing the decontamination device to the medical apparatus, as by securing the loop about a portion of the medical apparatus. In the case of a stethoscope, the loop 82 can be placed about the tubing of the stethoscope.

Indicia can be provided on the decontamination device to provide information about the decontamination device. For example, this indicia can indicate the type or size of medical apparatus for which the decontamination device is intended, the type of decontaminating compound in the dispenser, or the date by which the unit must be used. The indicia can be any suitable indicia, including the color of the housing 14 or printed or embossed alpha-numeric indicia 88, or any other suitable indicia, including graphical indicia, such as bar codes and the like.

In one aspect, the decontaminating compound is provided with an indicator to provide an indication that the medical apparatus has been decontaminated. This indicator compound can be a dye such as Red Dye #2.

The invention is suitable for many different medical apparatus. Any medical apparatus which comes into contact with more than one patient and has a contact surface suitable for decontaminating with the decontamination device can be used. It is only necessary that the housing of the decontamination device be adapted to receive the portion of the medical apparatus that is to be decontaminated.

Figure 7:
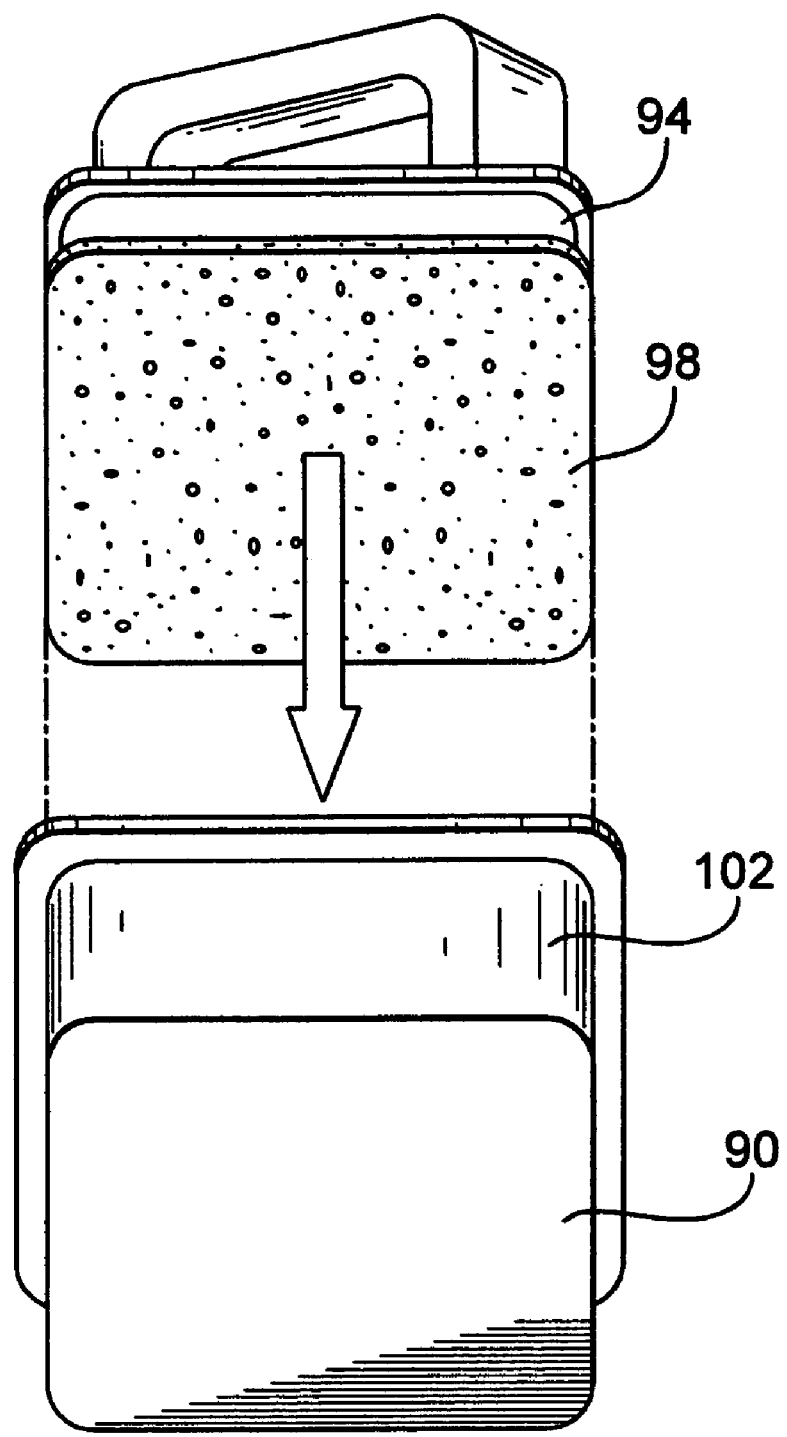
FIG. 7 is an exploded perspective illustrating the use of the decontamination device with defibrillator paddles.

There is shown in FIG. 7 a decontamination device 90 for use with a defibrillator paddle 94 having a contact surface 98. The housing 102 of the decontamination device 90 is dimensioned to receive a portion of the defibrillator paddle such that the contact surface 98 will come into contact with a dispenser within the housing 102.

The invention can be manufactured from suitable materials including plastics, metals, ceramics, and other materials. The invention is capable of taking on many different dimensions, designs, and constructions without departing from the spirit or essential attributes thereof. The invention also has utility with other types of apparatus other than medical apparatus which must be decontaminated prior to use. Accordingly, reference should be had to the following claims, rather than to the foregoing specification, as indicating the scope of the invention.

We claim:

1. A decontamination device for decontaminating medical apparatus, comprising:
    a housing;
    an absorbent pad carrying a decontaminating compound within said housing; and
    interlocking structure for removably engaging said housing to a portion of said medical apparatus, whereby said absorbent pad is placed into contact with said portion of said medical apparatus upon engagement and removed from contact upon disengagement, said interlocking structure comprising at least one elastically deformable, inwardly directed protrusion on said housing.

2. The decontamination device of claim 1, wherein said housing comprises a flexible portion to facilitate the removable engagement to said medical instrumentation.

3. The decontamination device of claim 1, further comprising additional means for attaching said housing to said medical apparatus.

4. The decontamination device of claim 3, wherein said additional means is a lanyard.

5. The decontamination device of claim 1, further comprising a removable cover for said housing.

6. The decontamination device of claim 1, wherein at least two of said housings are detachably engaged.

7. The decontamination device of claim 1, wherein said housing comprises indicia providing information concerning said decontamination device.

8. The decontamination device of claim 7, wherein said indicia comprises at least one selected from the group consisting of color, printed material, bar code, and embossed material.

9. The decontamination device of claim 7, wherein said indicia comprises at least one selected from the group consisting of the decontaminating compound and the medical apparatus for which the decontamination device is intended.

10. The decontamination device of claim 1, wherein said decontaminating compound comprises a disinfecting compound and a sterilizing compound.

11. The decontamination device of claim 1, wherein said decontaminating compound is at least one selected from the group consisting of glutaraldehydes.

12. The decontamination device of claim 1, wherein said decontaminating compound is at least one selected from the group consisting of chlorine compounds.

13. The decontamination device of claim 1, wherein said decontaminating compound is at least one selected from the group consisting of alcohols.

14. The decontamination device of claim 1, wherein said decontaminating compound is at least one selected from the group consisting of iodophors.

15. The decontamination device of claim 1, wherein said decontaminating compound is at least one selected from the group consisting of peroxygen compounds.

16. The decontamination device of claim 1, wherein said decontaminating compound is at least one selected from the group consisting of phenolics.

17. The decontamination device of claim 1, wherein said decontaminating compound is at least one selected from the group consisting of quaternary ammonium compounds.

18. The decontamination device of claim 1, wherein said dispenser contains an indicator compound for indicating that the medical apparatus has been contacted by said decontaminating compound.

19. The decontamination device of claim 1, wherein said housing is dimensioned to receive the head of a stethoscope.

* * * * *